(12) United States Patent
Shaw et al.

(10) Patent No.: US 10,391,264 B2
(45) Date of Patent: Aug. 27, 2019

(54) MEDICAL DEVICE WITH SELECTIVELY RETRACTABLE NEEDLE CAP

(71) Applicants: Retractable Technologies, Inc., Little Elm, TX (US); Thomas J. Shaw, Frisco, TX (US)

(72) Inventors: Thomas J. Shaw, Frisco, TX (US); Ni Zhu, Plano, TX (US)

(73) Assignee: Retractable Technologies, Inc, Little Elm, TX (US)

( * ) Notice: Subject to any disclaimer, the term of this patent is extended or adjusted under 35 U.S.C. 154(b) by 644 days.

(21) Appl. No.: 14/679,847

(22) Filed: Apr. 6, 2015

(65) Prior Publication Data

US 2015/0283329 A1 Oct. 8, 2015

Related U.S. Application Data

(60) Provisional application No. 61/975,569, filed on Apr. 4, 2014.

(51) Int. Cl.
*A61M 5/32* (2006.01)
*A61M 5/178* (2006.01)
*A61M 5/50* (2006.01)

(52) U.S. Cl.
CPC ......... *A61M 5/3234* (2013.01); *A61M 5/1782* (2013.01); *A61M 5/502* (2013.01); *A61M 2005/3239* (2013.01)

(58) Field of Classification Search
CPC .... A61M 5/32; A61M 5/3234; A61M 5/3202; A61M 5/1782; A61M 5/502; A61M 2005/3239; A61M 5/3243; A61M 5/508; A61M 5/322; A61M 5/3232; A61M 25/0612; A61M 2005/3247; A61M 5/3241; A61M 25/0618; A61M 25/0631
USPC ................................ 604/110, 195, 198, 263
See application file for complete search history.

(56) References Cited

U.S. PATENT DOCUMENTS

2006/0253074 A1* 11/2006 Thayer ................ A61M 5/3234
 604/110
2007/0276338 A1* 11/2007 Shue .................... A61M 5/3202
 604/187
2010/0292654 A1* 11/2010 Schraga ................ A61M 5/326
 604/198

FOREIGN PATENT DOCUMENTS

WO WO 2013050475 A2 * 4/2013 ............ A61M 5/326

* cited by examiner

*Primary Examiner* — Imani N Hayman
*Assistant Examiner* — Tiffany Legette
(74) *Attorney, Agent, or Firm* — Ross Barnes LLP; Monty L. Ross (57) ABSTRACT

A medical device having a forwardly-projecting needle and a selectively-movable needle cap that can be variously positioned to cover all or a portion of the needle, depending upon whether the device is, for example, being transported, aspirated or used to inject a therapeutic fluid. The device can optionally be configured to enable retraction of the needle into the body for safe disposal following use.

10 Claims, 14 Drawing Sheets

MEDICAL DEVICE WITH SELECTIVELY RETRACTABLE NEEDLE CAP

FIELD OF THE INVENTION

This invention relates to a medical device and more particularly to a medical device such as a non-reusable syringe having a hypodermic needle, preferably a retractable needle, and a needle cap that can be selectively retracted and then repositioned during use to suit the stage of operation of the device prior to patient injection or needle retraction.

DESCRIPTION OF RELATED ART

Accidental needle sticks and the resultant transmission of blood-borne illnesses are a principal cause of concern to medical workers who must handle medical devices such as syringes in all aspects of their use, from unpackaging to disposal, many times per day. Medical devices having forwardly projecting needles are typically provided with a protective needle cap that is removable prior to use. Following use of a device, depending upon its design and construction, the needle is desirably retracted into a position where the needle tip is no longer exposed, thereby preventing reuse. Health care workers are typically cautioned against recapping exposed needles with the protective needle cap following use because of the associated risk of needle stick injury. In some devices, pivotable guards or forwardly slidable sheaths are sometimes provided to cover the needle tip following use and prior to disposal of the device, although those devices also have disadvantages and fail to eliminate needle stick risks. Medical devices with used needles are often simply deposited into "sharps" disposal containers, although this procedure also presents disease risks to health care workers, patients, and downstream handlers of the disposed devices.

During a typical injection sequence using a conventional hypodermic syringe, for example, the syringe is removed from its sterile packaging and the protective needle cap is removed and either dropped into a trash receptacle or set aside by the health care worker performing the injection. The syringe is then manipulated by the user to insert the exposed needle into a vial to aspirate a desired fluid dosage into the barrel. During aspiration, and depending upon the size of the vial, the length of the exposed portion of the needle, and the angle of insertion, the needle tip can sometimes contact the bottom or side wall of the vial, thereby bending the needle or blunting the needle tip.

Also, it is not uncommon for a health care worker to draw an injection and then lay the filled syringe down with an uncovered, exposed needle prior to administering the injection. This can occur, for example, where the user lays the syringe down on a tray, table or other surface for a moment while swabbing the injection site or attending to some other matter prior to the injection. During any such occurrence, the needle and needle tip are exposed, with an attendant risk of accidental needle stick to the worker or patient, or accidental contamination of the needle by contact with an unsterile surface prior to the injection.

A medical device having a forwardly projecting needle is therefore needed that comprises a needle cap or needle cover configured to protect the needle tip prior to use and that can be selectively moved to an alternate position exposing the needle tip and a portion of the needle for some clinically desirably purpose during use. The subject needle cap or needle cover will also desirably be completely removable from the device and disposable prior to use of the device for injecting a therapeutic fluid, and will preferably comprise a retractable needle that is no longer in a forwardly projecting, exposed position following use. The capability for complete removal of the needle cover during administration is desirable so as to clear the site from all unnecessary visual obstructions and provide for safer operation.

SUMMARY OF THE INVENTION

The invention disclosed here is a safe and reliable medical device having a forwardly projecting, preferably retractable, needle and a needle cap that protects the needle from damage or contamination by contact prior to use, that can be selectively retracted to expose a portion of the needle during use, and that can be subsequently repositioned or removed completely during use and prior to needle retraction. Although the invention is primarily described herein in the embodiment of a hypodermic syringe used for injecting a therapeutic fluid directly into a patient, it will be appreciated upon reading this disclosure that similar benefits and advantages are also achievable where the subject medical device is used for injecting into a fluid access port or otherwise configured for other medical applications. The subject invention desirably comprises only a few parts, all of which are easily manufactured and assembled and do not require close tolerances, thus facilitating large volume, low cost production.

A distinguishing feature of the disclosed invention is a needle cap for a medical device having a forwardly projecting needle, in which the needle cap can be selectively disposed in at least the three following positions, depending on the mode or stage of operation of the device: A pre-use position in which a portion of the needle cap extends forwardly past and circumferentially surrounds the forwardly projecting needle tip; an intermediate position in which the needle cap is moved rearwardly relative to the needle to expose the needle tip and a desired portion of the overall length of the needle; and a final position in which the needle cap is removed entirely from the medical device and is no longer needed.

In one embodiment, the subject needle cap is desirably hollow and generally cylindrical with both ends open, is releasably attachable in a first position relative to a front portion of a medical device, is configured to be moveable rearwardly from the first position to a second position relative to the front portion of the medical device to expose a portion of a forwardly extending needle for a clinical procedure such as aspirating a therapeutic fluid, is forwardly movable back to the first position following the clinical procedure to recap and protect the needle, and is completely releasable and removable from the device prior to a clinical procedure such as administering an injection. Where the medical device is also provided with a needle retraction mechanism, the needle can be retracted following completion of the clinical procedure to prevent re-use or accidental needle sticks.

In one embodiment of the subject medical device, the selectively retractable needle cap and the body comprise cooperatively configured interfering structures that resist premature or unintended rearward sliding movement of the needle cap relative to the body.

In one embodiment of the subject medical device, the selectively retractable needle cap and the body comprise cooperatively-configured interfering structures that resist accidental or premature separation of the needle cap from the body.

In one embodiment of the subject medical device, the selectively retractable needle cap comprises manually-operated latch features configured to resist premature or accidental movement or removal of the needle cap until the latch features are released by the user.

BRIEF DESCRIPTION OF THE DRAWINGS

The apparatus of the invention is further described and explained in relation to the following drawings wherein.

DESCRIPTION OF THE PREFERRED EMBODIMENTS

Figure 1:
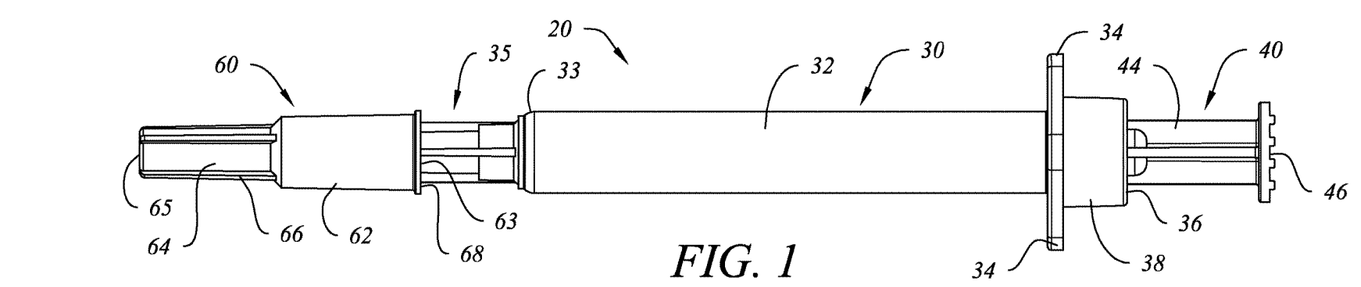
FIG. 1 is a side elevation view of one embodiment of the subject medical device with a needle cap covering a forwardly projecting needle.
Figure 2:
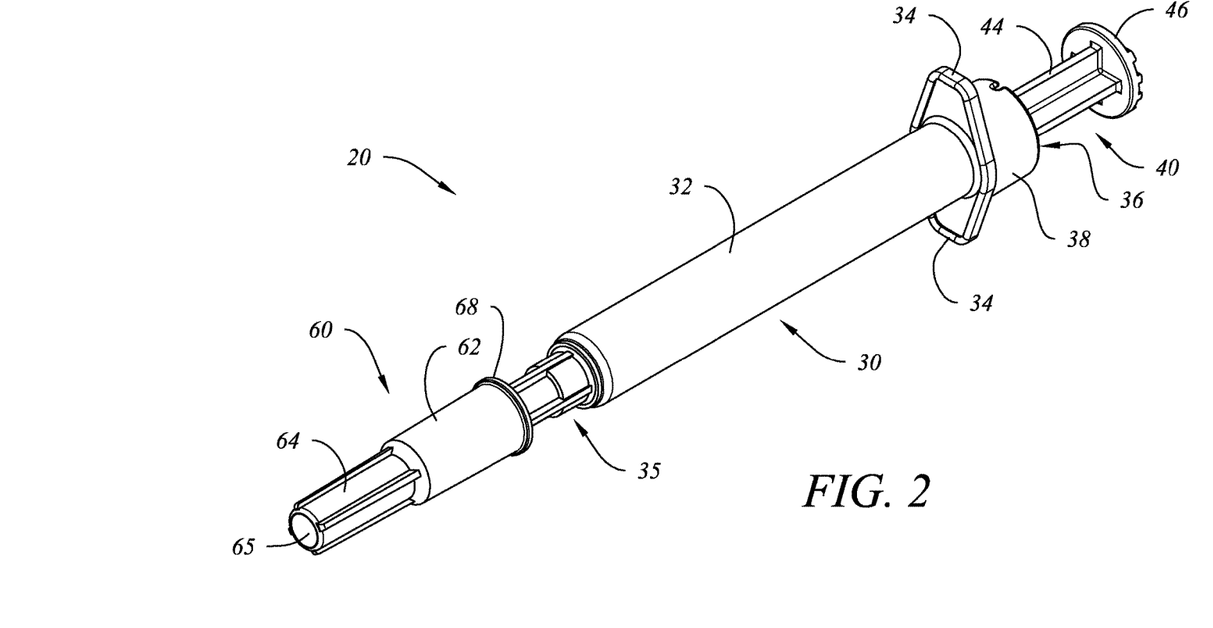
FIG. 2 is a front perspective view of the device as depicted in FIG. 1.
Figure 3:
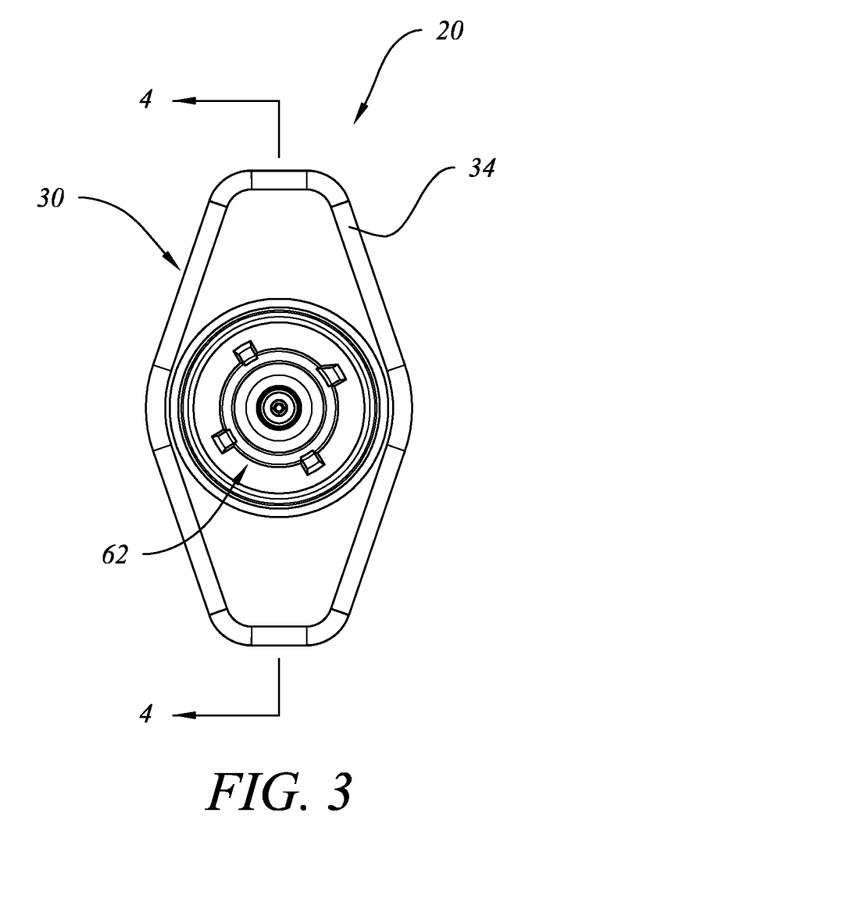
FIG. 3 is a front elevation view of the device of FIG. 1.

Referring to FIG. 1, a medical device 10 is illustrated in this embodiment as syringe 20. Although medical device 10 can take many different forms, a syringe having a retractable needle as further disclosed and described, for example, in U.S. Pat. No. 7,351,224 is believed to be useful for practicing the present invention after being specially adapted consistent with the teachings of this specification and the accompanying drawings.

Syringe 20 is desirably shipped in a sterile package that is opened shortly before use. Upon removal from the package, syringe 20 will initially be configured substantially as depicted in FIGS. 1-5. Syringe 20 comprises as its principal parts barrel 30, plunger 40, needle assembly 50 and needle cap 60. Barrel 30 desirably comprises an elongate tubular bore 32 with a forwardly facing annular shoulder 33, oppositely disposed transversely projecting finger flanges 34, a forwardly facing nozzle tube 35 and a rearwardly facing opening 36 surrounded by substantially cylindrical collar 38.

Figure 6:
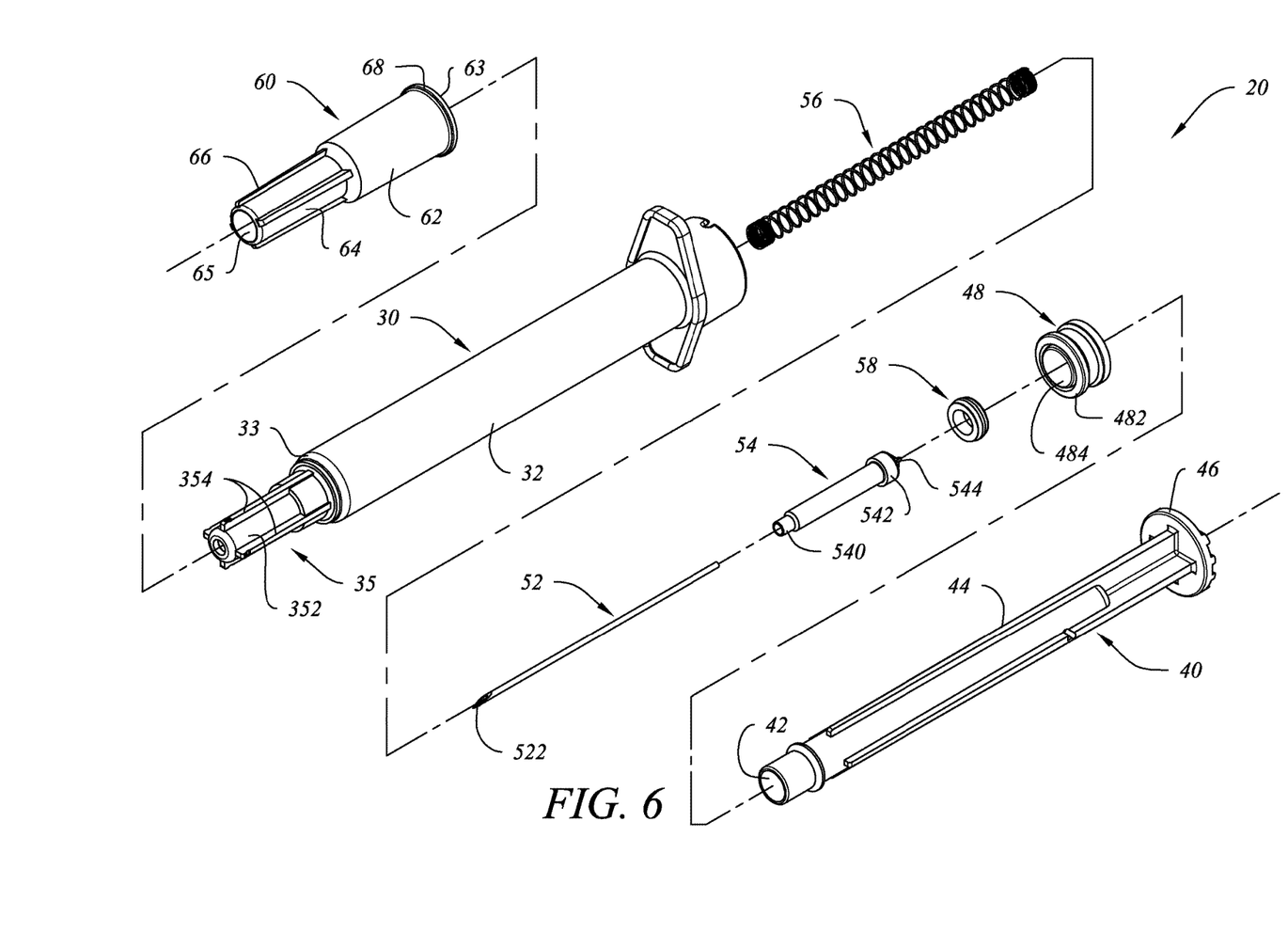
FIG. 6 is an exploded perspective view of device of FIG. 2.

Plunger 40 comprises a forward portion 41 (see FIG. 4) which is initially positioned within barrel 30, a rearward portion 44 extending beyond cylindrical collar 38 and a thumb grip 46. Referring to FIG. 6, plunger 40 also comprises needle retraction cavity 42 and plunger seal 48. Plunger seal 48 further comprises annular sealing ring 482 and elastomeric web 484. Rearwardly facing thumb grip 46 is desirably provided opposite elastomeric web 484 for use in moving plunger 40 in coaxial sliding relationship to the inside wall of barrel 30 during use of syringe 20. Plunger 40 is desirably moved rearwardly relative to barrel 30 to draw a therapeutic fluid into barrel 30 and is moved forwardly relative to barrel 30 to expel a therapeutic fluid from syringe 20.

In the initial position illustrated in FIGS. 1-5, needle assembly 50 is covered by needle cap 60. However, components of needle assembly 50 are illustrated in FIG. 6. Needle assembly 50 comprises needle 52, with needle tip 522; needle holder 54, further comprising rearward annular ring 542 and rearwardly-facing head 544; retraction spring 56; and toroidal retainer member 58.

Needle cap 60 preferably comprises hollow body 62 and tapered nose tube 64, which is surrounded by a plurality of circumferentially spaced, longitudinally extending ribs 66. A rearward end of hollow body 62 comprises an annular rib 68. A preferred embodiment of needle cap 60 is distinguished from typical prior art devices by comprising both a rearward opening 63 and forward opening 65.

Figure 5:
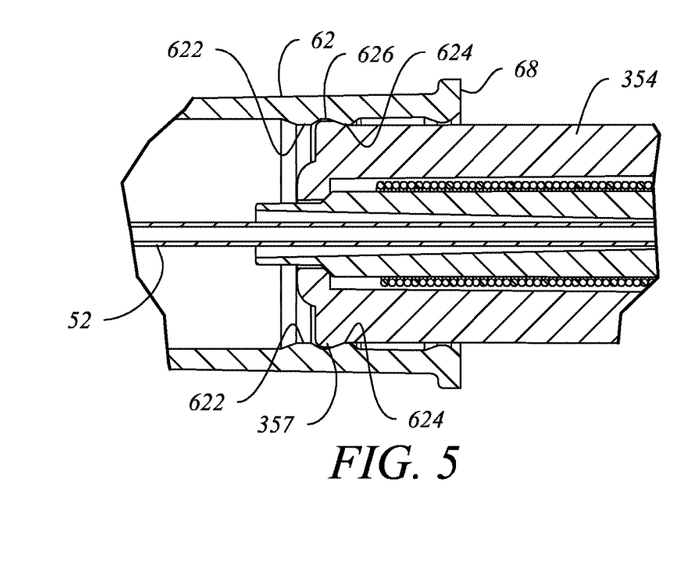
FIG. 5 is a detail view of the area identified as "5" within FIG. 4.

Referring to FIG. 5, additional components of needle cap 60 and barrel 30 are visible in cross section. A forward annular inward projection 622 and a rearward annular inward projection 624 are disposed on the inside wall of hollow body 62 and desirably define annular recess 626 between them. An annular outward projection 357 is disposed on the outside surface of nozzle tube 35. Annular inward projections 622, 624 and recess 626 are configured to cooperate with annular outward projection 357 of nozzle tube 35 to form a detent mechanism that provides resistance tending to prevent needle cap 60 from sliding forwardly relative to nozzle tube 35 (and becoming disengaged from barrel 30) or from sliding rearwardly (and prematurely exposing needle tip 522) prior to use of syringe 20.

In FIGS. 1-5, needle cap 60 is illustrated in its pre-use position where nose tube 64 of needle cap 60 is preferably configured to extend forwardly beyond needle 52 and needle tip 522. In this position needle cap 60 helps protect needle tip 522 from damage or contamination by contact prior to use and helps protect health care workers and patients from accidental needle sticks and the associated risk of infection or disease.

With conventional syringes and needle caps, the needle cap must be completely removed from the syringe to perform any procedure using the needle, including, for example, aspirating a therapeutic fluid from a vial. As the needle is inserted into a vial, the full length of the forwardly projecting part of the needle is exposed. As a result, the needle can be easily contaminated, bent, or damaged by contact with the inside wall or inside bottom surface of the vial.

Figure 7:
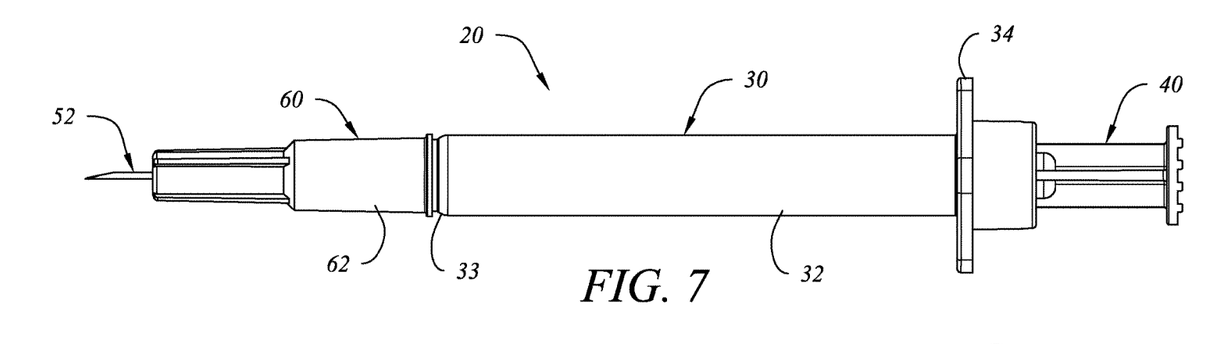
FIG. 7 is the side elevation view of the device of FIG. 2 with the needle cap in the retracted position.
Figure 8:
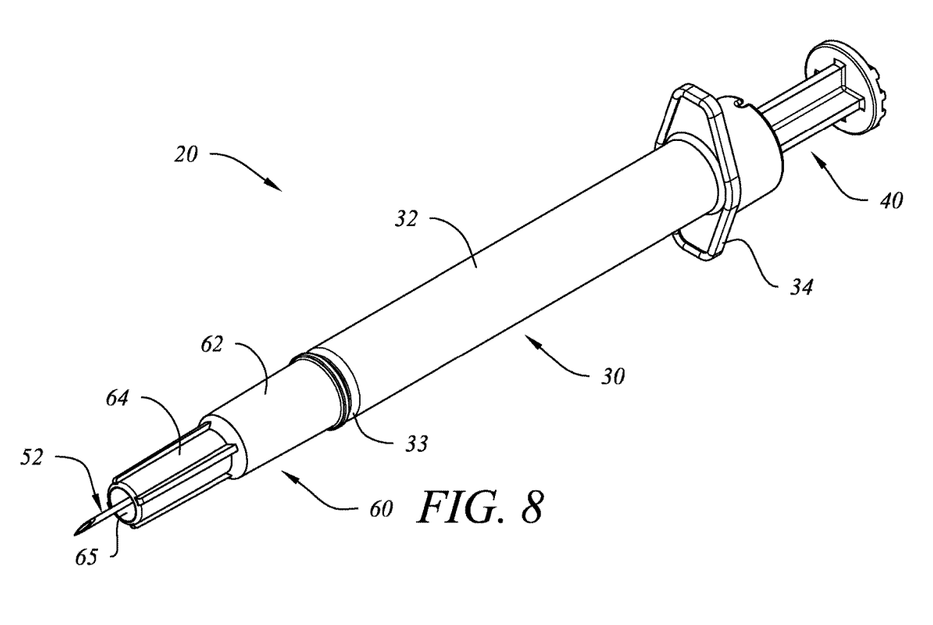
FIG. 8 is a front perspective view of the device as in FIG. 7.
Figure 9:
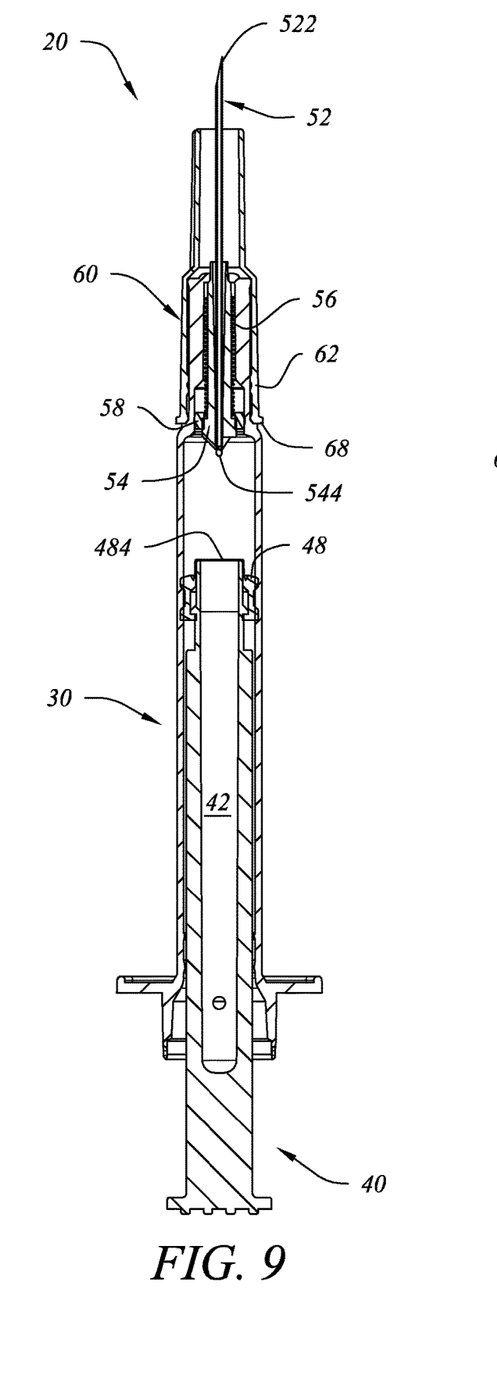
FIG. 9 is a cross-sectional side elevation view of the device of FIG. 7.

FIGS. 7-9 illustrate one significant advantage of the present invention that is made possible by the fact that needle cap 60—unlike most syringe caps—is desirably open on both ends. With two open ends, it becomes possible to move needle cap 60 rearwardly relative to nozzle tube 35 to expose needle tip 522 and a portion of needle 52 during a procedure such as aspirating a therapeutic fluid into barrel 30. A user (not shown) can grasp needle cap 60 and move it rearwardly relative to nozzle tube 35 until rearward open end 63 of needle cap 60 contacts and abuts forwardly facing annular shoulder 33 of barrel 30, thereby simultaneously exposing the needle tip 522 and a portion of needle 52 sufficient to permit aspiration into barrel 30 without fully exposing all of needle 52.

Figure 10:
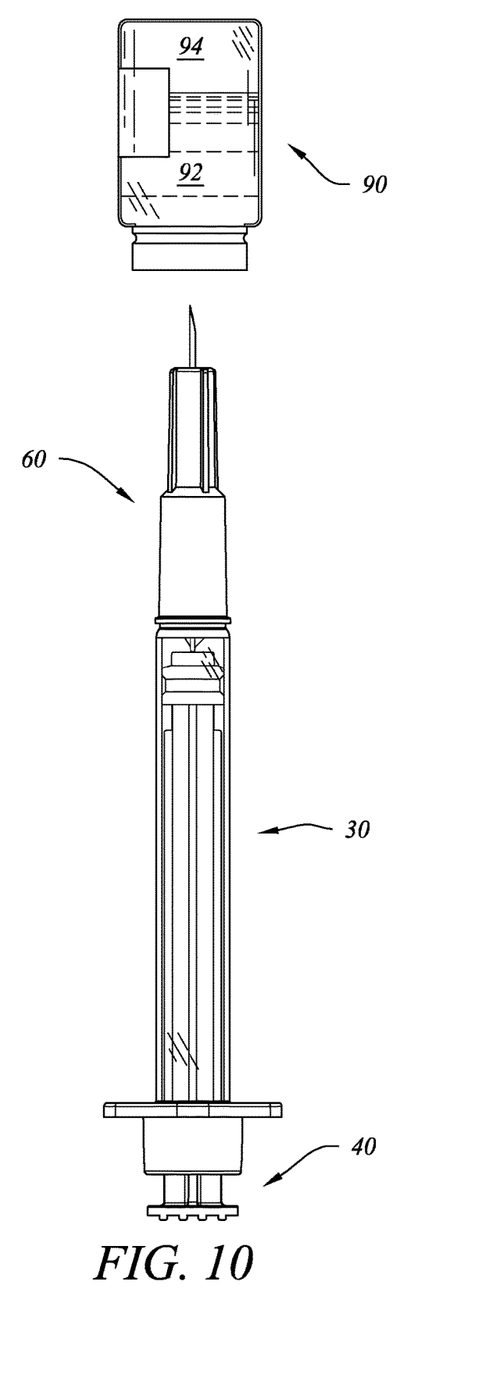
FIG. 10 is a side elevation view of the device of FIG. 7 with a vial of therapeutic fluid and a transparent barrel.
Figure 11:
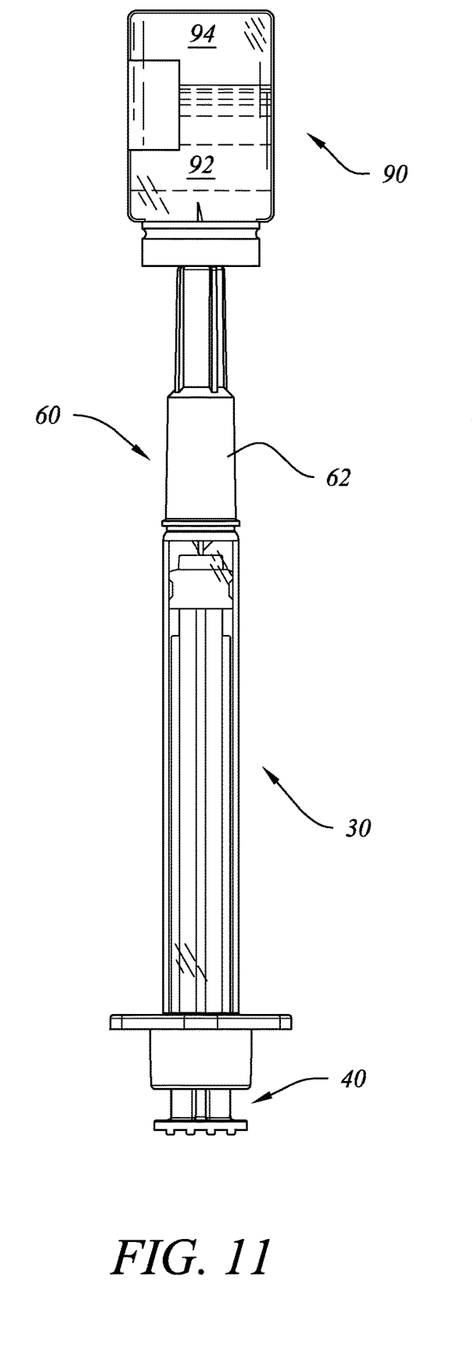
FIG. 11 is a side elevation view of the device of FIG. 10 with a needle inserted into the vial.
Figure 12:
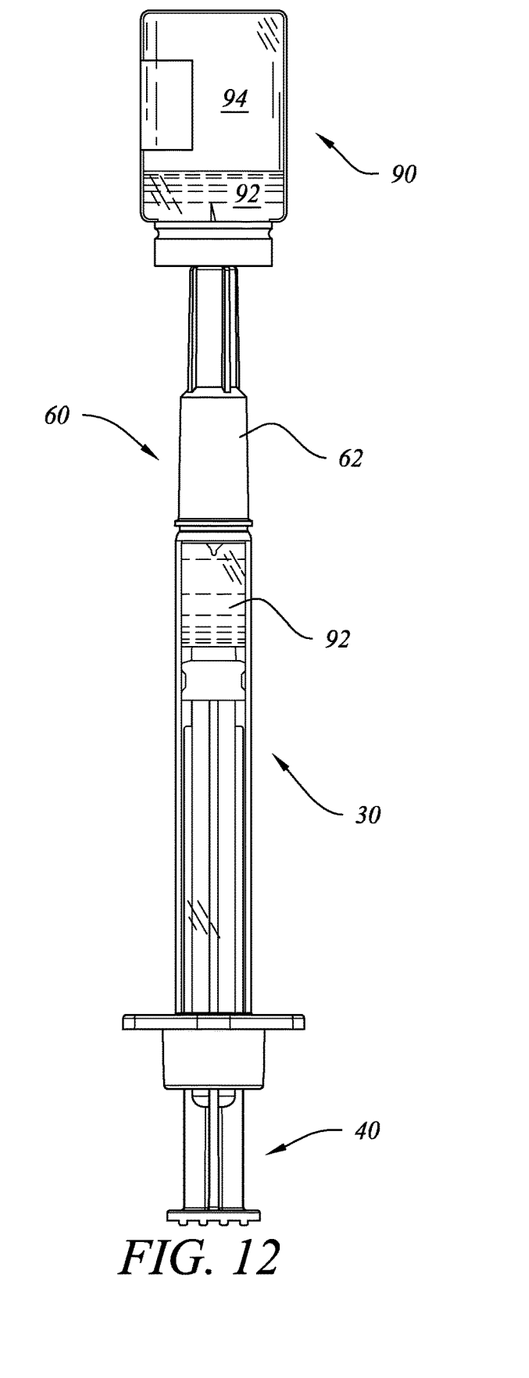
FIG. 12 is a side elevation view of the device of FIG. 11 showing therapeutic fluid being drawn into the barrel.

As shown in FIGS. 10-12, the user can then insert the exposed portion of needle 52 into a vial 90 to aspirate therapeutic fluid 92 into barrel 30 by moving plunger 40 rearwardly. By limiting the extent to which the forwardly projecting portion of the needle is exposed, the risk of damage to the needle is greatly reduced. Also, because vials are typically inverted during aspiration, limiting the extent of needle exposure means the user is less likely to inadvertently draw air into barrel 30 where the vial is only partially full of therapeutic fluid 92 and also contains an airspace 94.

Figure 13:
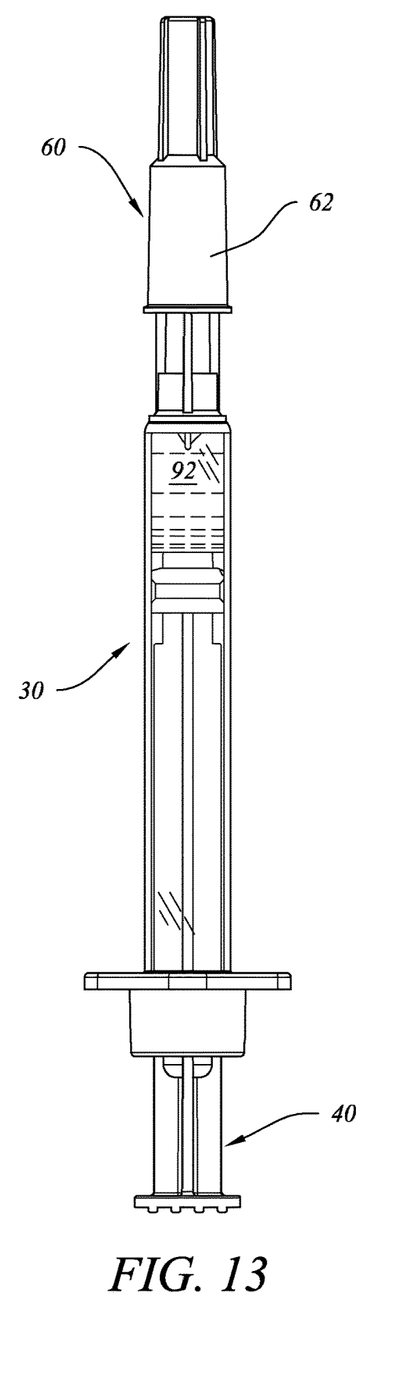
FIG. 13 is a side elevation view of the device of FIG. 12 showing therapeudic fluid in the barrel and the needle cap having been returned to its initial position.

Following aspiration, and referring to FIG. 13, the needle cap can be returned to its original position by grasping hollow body 62 and moving it forwardly relative to nozzle tube 35 until it again reaches the original position, where it is held by the detent mechanism previously described. In this state, syringe 20 contains therapeutic fluid 92 but needle 52 and needle tip 522 are protected by needle cap 60 while awaiting injection.

Figure 14:
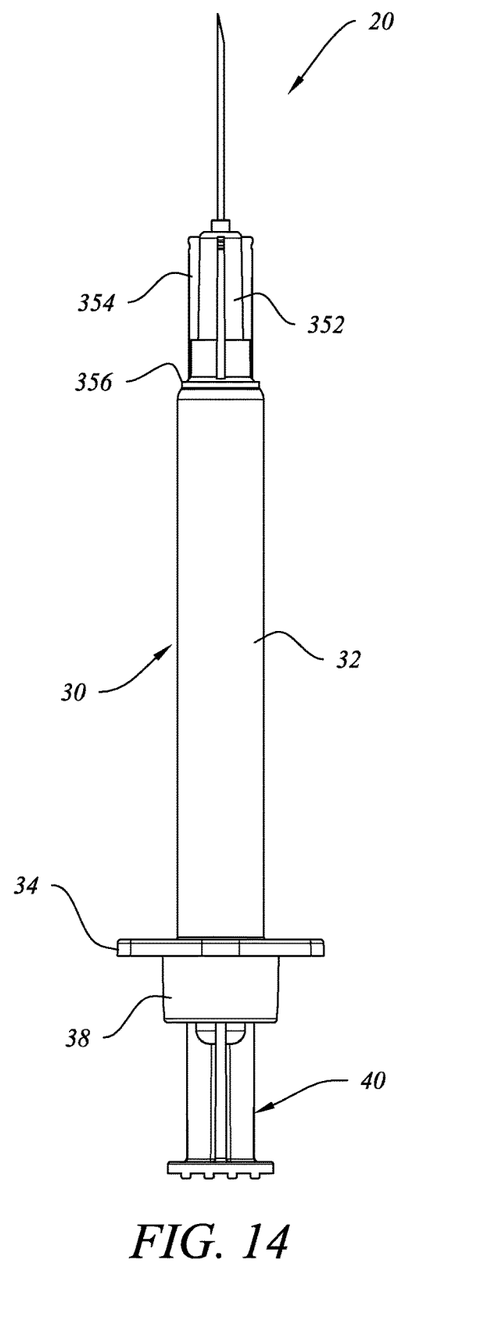
FIG. 14 is a side elevation view of the device of FIG. 7 with the needle cap removed.

Referring to FIG. 14, when the user is ready to perform an injection, needle cap 60 can be completely removed from the front of syringe 20 by grasping hollow body 62 and carefully moving needle cap 60 forwardly relative to nozzle tube 35 with sufficient force to overcome the detent mechanism. The needle cap 60 can be discarded if a retractable needle syringe is being used, since needle 52 will retract into retraction cavity 42 after injection.

Figure 15:
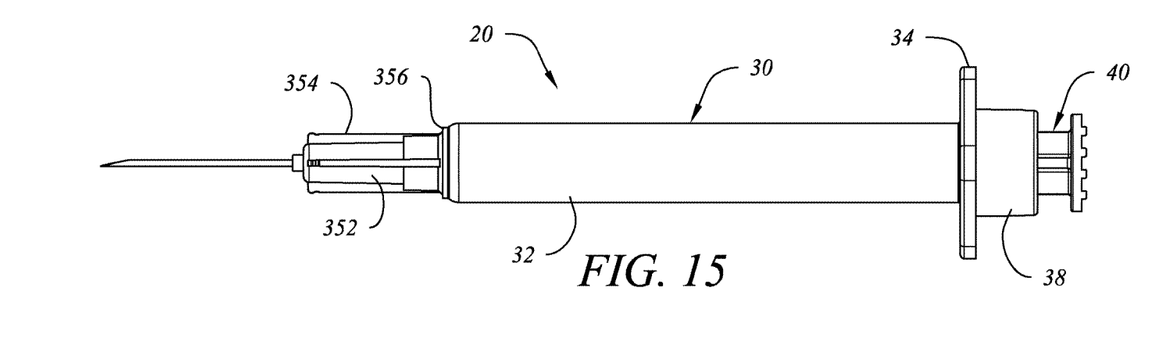
FIG. 15 is a side elevation view of the device of FIG. 14 near the completion of an injection.
Figure 16:
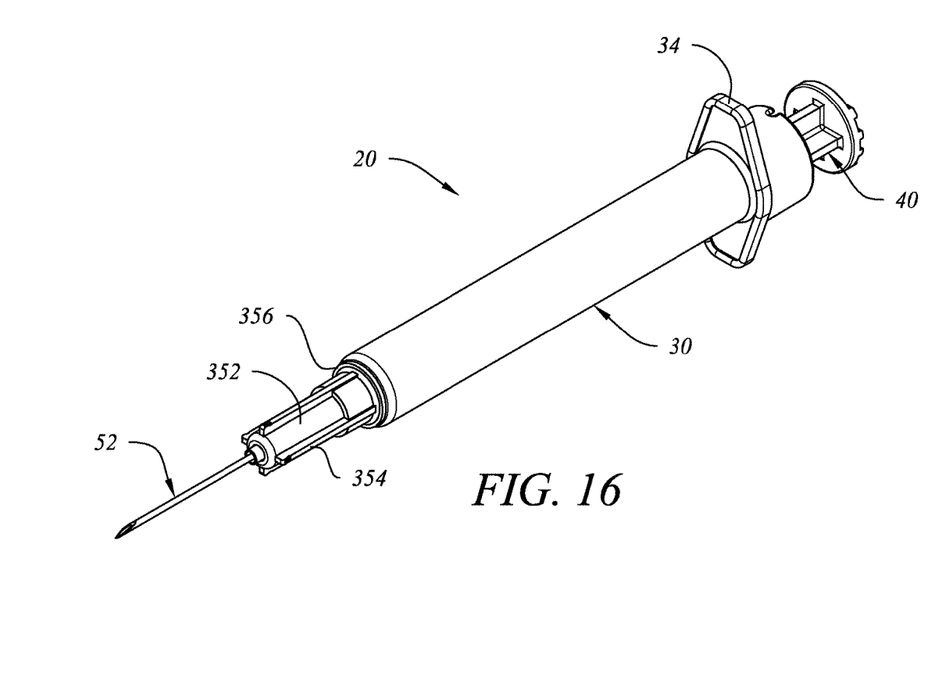
FIG. 16 is a front perspective view of the device of FIG. 15.
Figure 17:
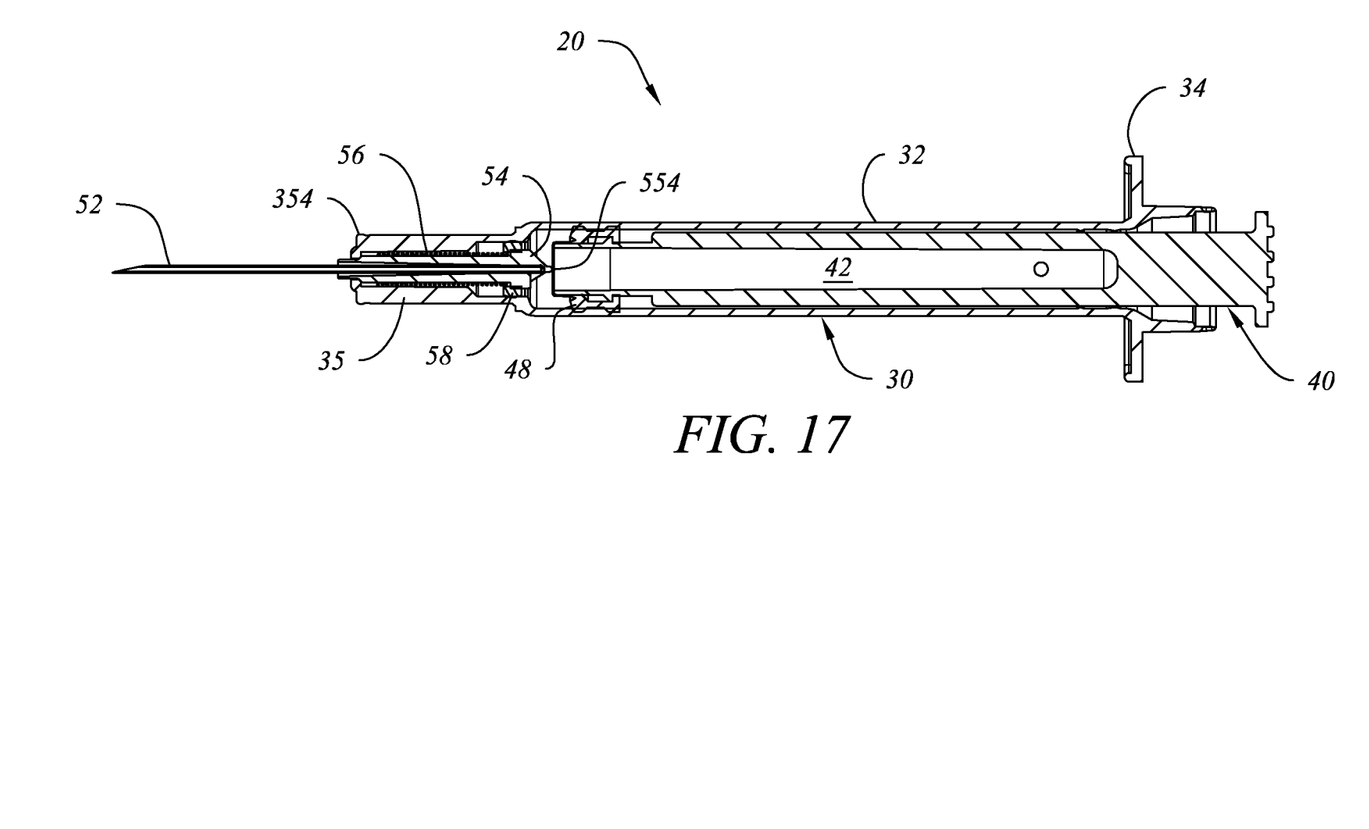
FIG. 17 is a cross-sectional side elevation view of the device of FIG. 15.
Figure 18:
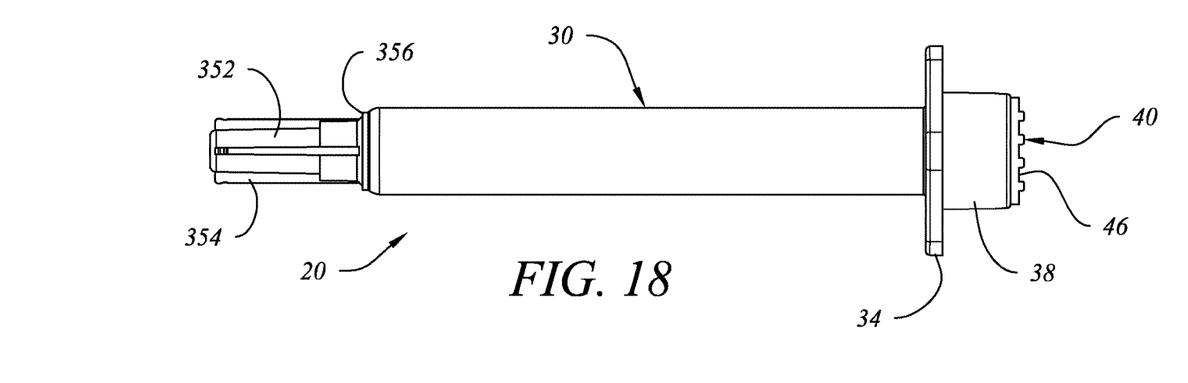
FIG. 18 is a side view of the device of FIG. 15 with the needle retracted into the body of the syringe.

Figures FIGS. 15-17 illustrate syringe 20 with needle cap 60 removed, in the process of in injection. At this stage, plunger 40 has been advanced almost to the point of completing the injection, Further forward movement of plunger 40 will complete the injection and initiate retraction of needle 52 as described below.

Referring again to FIGS. 4-6, a preferred needle retraction mechanism for syringe 20 is illustrated. Needle holder 54 is seated inside nozzle tube 35 of syringe 20. In an initial position, needle retraction spring 56 is compressed in an annular space defined between the outside of needle holder 54 and the inside wall of nozzle tube 35. Needle retraction spring 56 is held in compression by toroidal retainer member 58 disposed around the rearwardly facing head 542 of needle holder 54. In an initial condition of plunger 40, annular sealing ring 482 and a transversely disposed elastomeric web 484 prevent fluid from entering needle retraction cavity 42 defined inside plunger 40.

Figure 4:
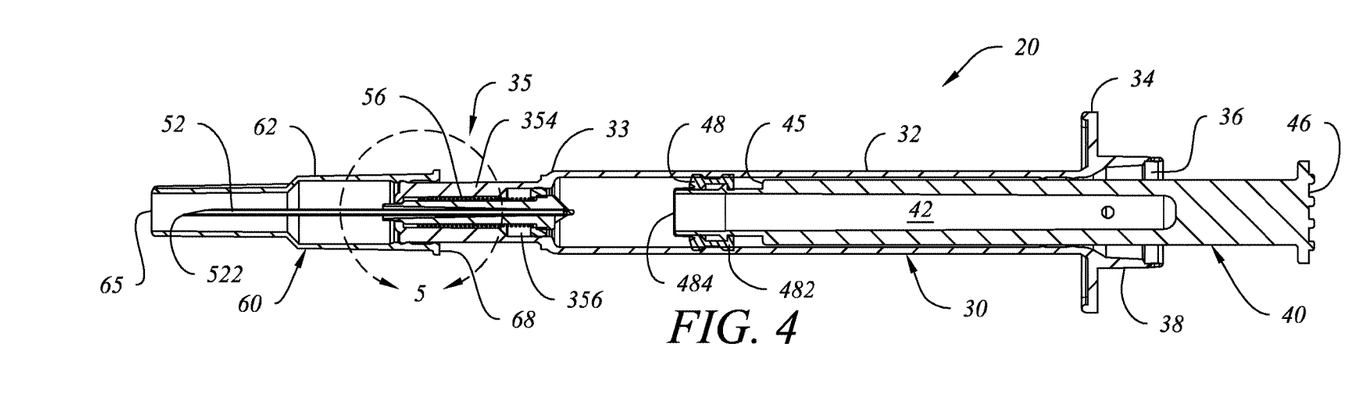
FIG. 4 is a cross-sectional side elevation view along line 4-4 of FIG. 3.

After therapeutic fluid is expelled, continued forward movement of plunger 40 relative to barrel 30 and will cause elastomeric web 484 to contact pointed head 544 of needle holder 54. This contact will cause pointed head 544 to stretch and then puncture elastomeric web 484. The continued forward movement of plunger 30 also forces toroidal retainer member 58 forwardly into annular space 356 inside nozzle tube 35. The forward movement of retainer member 58 into annular space 356 allows the rearwardly-directed biasing force of compressed spring 56 to drive needle holder 54 rearwardly into needle retraction cavity 42 of plunger 40, thereby causing needle 52 to retract. After needle 52 has been retracted into retraction cavity 42, syringe 20 is ready for disposal into a suitable receptacle (not shown).

Figure 19:
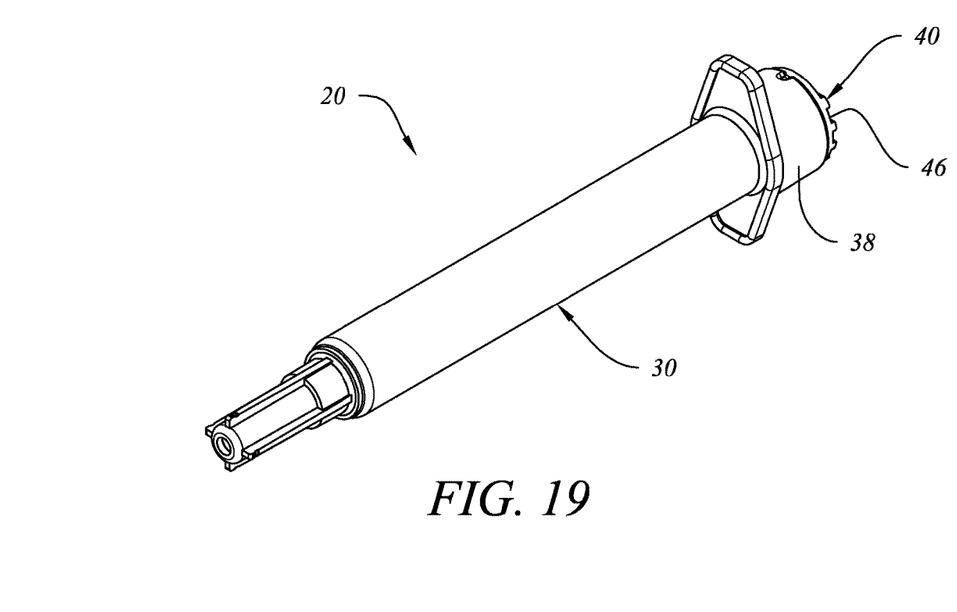
FIG. 19 is a front perspective view of the device of FIG. 18.
Figure 20:
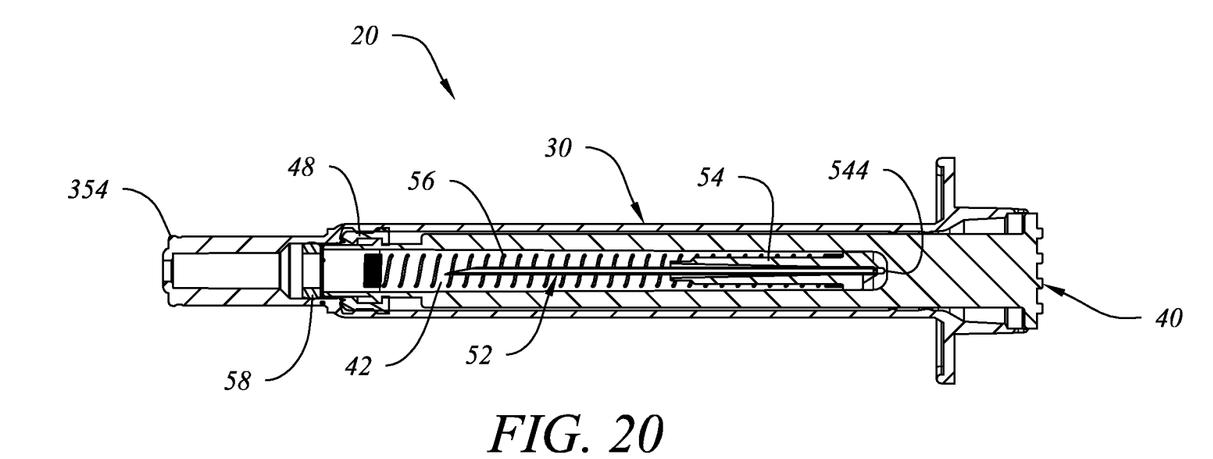
FIG. 20 is a cross-sectional side elevation view of the device of FIG. 18.
Figure 21:
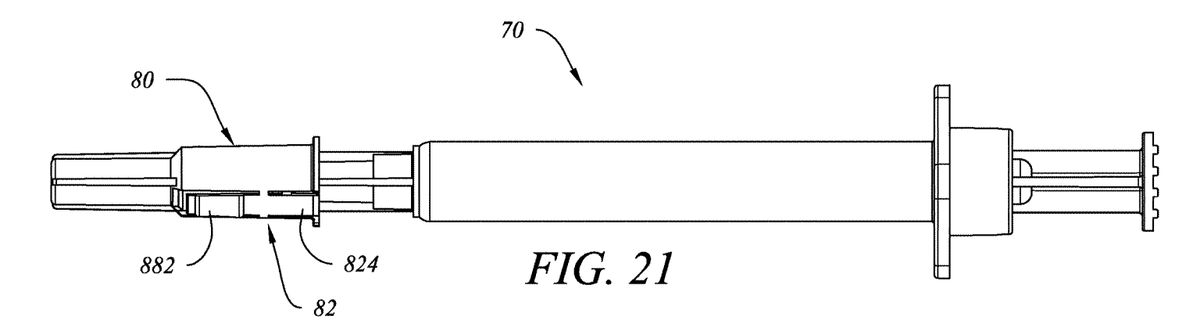
FIG. 21 is a side elevation view of another embodiment of the subject medical device with the needle cap covering a forwardly projecting needle.
Figure 22:
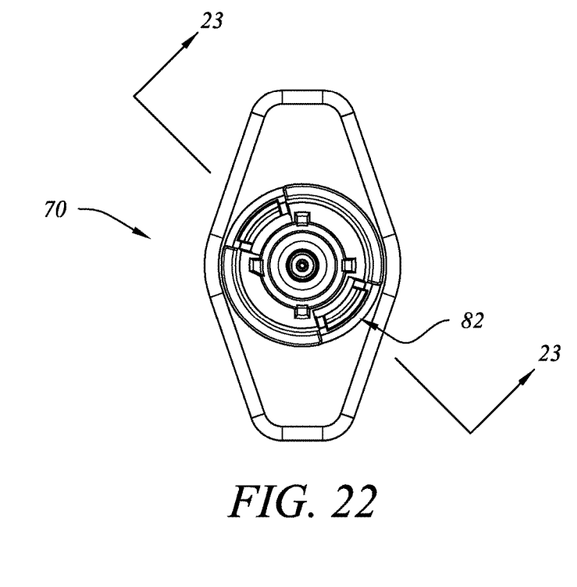
FIG. 22 is a front elevation view of the device of FIG. 21.
Figure 23:
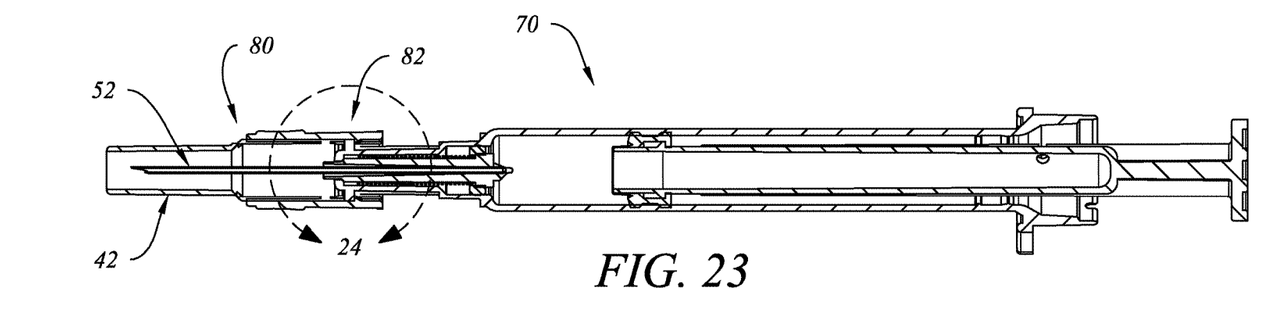
FIG. 23 is a cross-section view taken along line 23-23 of FIG. 22.
Figure 24:
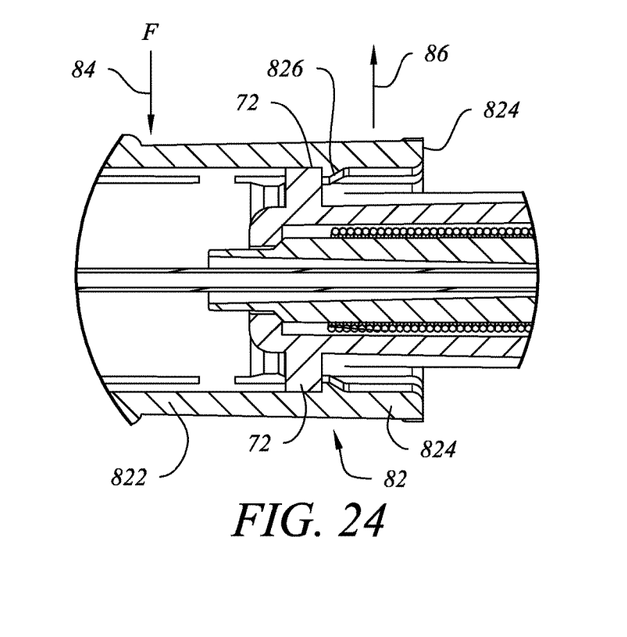
FIG. 24 is a detail view of the area identified as "24" within FIG. 23.

FIGS. 21-24 illustrate another embodiment of the invention. In this embodiment needle cap 80 comprises a fulcrum mechanism 82 which further comprises finger pads 822 near its forward end and cap release latches 824 near its rearward end. Referring to FIG. 19, depressing finger pads 822 as indicated by arrow 84 causes cap release latches 824 to flex outwardly as indicated by arrow 86. The outward movement of cap release latches 824 allows inwardly facing projection 826 to clear blocking member 72 disposed on or near the front end of syringe barrel 70 and allows removal of needle cap 80 from syringe barrel 70. Otherwise, this embodiment will be seen by those of ordinary skill in the art to function much as previously described for the prior embodiment.

Other alterations and modifications of the invention will likewise become apparent to those of ordinary skill in the art upon reading this specification in view of the accompanying drawings, and it is intended that the scope of the invention disclosed herein be limited only by the broadest interpretation of the appended claims to which the inventor(s) and/or Applicant are legally entitled.

What is claimed is:

1. A syringe useful for injecting an aspirated therapeutic fluid, the syringe comprising in combination:
   a barrel having an inside wall;
   a plunger disposed in coaxial sliding relationship to the inside wall;
   a needle assembly further comprising a rearwardly biased needle holder and a forwardly-projecting needle and needle tip that is are retractable into the barrel following injection of the therapeutic fluid; and
   a needle cap further comprising a hollow body and tapered nose tube with oppositely disposed proximal and distal open ends;
   wherein the needle cap is configured to be selectively moveable between a pre-use position in which a portion of the needle cap releasably engages the barrel and extends forwardly past and circumferentially surrounds the forwardly projecting needle tip, an intermediate position in which the needle cap is moved rearwardly relative to the barrel to expose the needle tip and a forwardly extending portion of the needle sufficiently to allow the therapeutic fluid to be aspirated from a vial into the barrel by moving the plunger rearwardly inside the barrel after inserting the needle tip into the vial; and
   wherein the needle cap is configured to be selectively moveable forwardly from the intermediate position back to the pre-use position following aspiration to recap and protect the needle and needle tip pending injection of the therapeutic fluid; and
   wherein the needle cap is configured to be moveable forwardly from the pre-use position to a final position in which the needle cap is completely released and removed from the barrel to fully expose the needle forwardly of the barrel prior to injecting the aspirated therapeutic fluid by expelling the therapeutic fluid from the barrel.

2. The syringe of claim 1 wherein the needle cap and barrel are frictionally engaged when the needle cap is in the pre-use position.

3. The syringe of claim 1 wherein the rearwardly biased needle holder further comprises a rearwardly facing, pointed head configured to puncture a transverse elastomeric web blocking access into a needle retraction cavity disposed inside the plunger when the plunger is moved fully forward inside the barrel to complete injection of the therapeutic fluid.

4. The syringe of claim 1 wherein the barrel further comprises a blocking structure that limits rearward sliding movement of the needle cap relative to the barrel as the needle cap reaches the intermediate position.

5. The syringe of claim 4 wherein the blocking structure is a forwardly facing annular shoulder configured to abut against a cooperatively configured, rearwardly facing shoulder of the needle cap.

6. The syringe of claim 1 wherein the needle cap comprises a first interfering structure and the barrel comprises a second interfering structure, the first and second interfering structures being cooperatively configured to form a detent mechanism that resists forward or rearward sliding movement of the needle cap relative to the barrel when the needle cap is in the pre-use position.

7. The syringe of claim 6 wherein the needle cap is graspable while disposed in the pre-use position and is rearwardly moveable relative to the barrel from the pre-use position to the intermediate position by an application of manual force to overcome resistance of the detent mechanism and expose the needle tip and a forwardly extending portion of the needle.

8. The syringe of claim 6 wherein the needle cap further comprises finger pads against which opposed forces are applied to overcome the resistance provided by the detent mechanism.

9. The syringe of claim 6 wherein at least one of the first and second interfering structures is an annular projection.

10. The syringe of claim 9 wherein another of the first and second interfering structures is an annular recess.

* * * * *